United States Patent [19]
Veitch

[11] Patent Number: 4,690,569
[45] Date of Patent: Sep. 1, 1987

[54] THERMAL PROFILE SYSTEM

[75] Inventor: Randall C. Veitch, Allentown, Pa.

[73] Assignee: Qualtronics Corporation, Palm, Pa.

[21] Appl. No.: 865,761

[22] Filed: May 22, 1986

[51] Int. Cl.⁴ ............................................ G01N 25/00
[52] U.S. Cl. ........................................ 374/11; 374/12; 374/121; 432/43; 364/557
[58] Field of Search .................. 374/10, 11, 12, 121, 374/124, 137, 45; 236/1 C; 237/2 R, 2 A, 12; 432/51, 241, 43, 45, 46, 18, 19, 24; 364/557, 578, 579, 580

[56] References Cited

U.S. PATENT DOCUMENTS

| | | | |
|---|---|---|---|
| 3,392,570 | 7/1968 | Bonjour et al. | 374/11 |
| 3,888,621 | 6/1975 | Williams | 432/45 |
| 3,982,882 | 9/1976 | Weingrad | 432/43 |
| 4,333,332 | 6/1982 | Privalov | 374/10 |
| 4,461,616 | 7/1984 | Vukovich, Jr. | 432/43 |
| 4,541,730 | 9/1985 | Comey et al. | 374/12 |
| 4,588,124 | 5/1986 | Takata et al. | 237/2 A |
| 4,610,628 | 9/1986 | Mizushina | 432/241 |

Primary Examiner—Steven L. Stephan
Assistant Examiner—Patrick R. Scanlon
Attorney, Agent, or Firm—Sanford J. Piltch

[57] ABSTRACT

Apparatus and method for implementing a characterized thermal profile upon a temperature/time dependent process on any material or materials susceptible to such thermal processing in accordance with a closed loop environmental feedback system and a corresponding predetermined characterized thermal profile.

14 Claims, 15 Drawing Figures

INITIALIZATION
AND USER PROGRAM
MODE ROUTINES

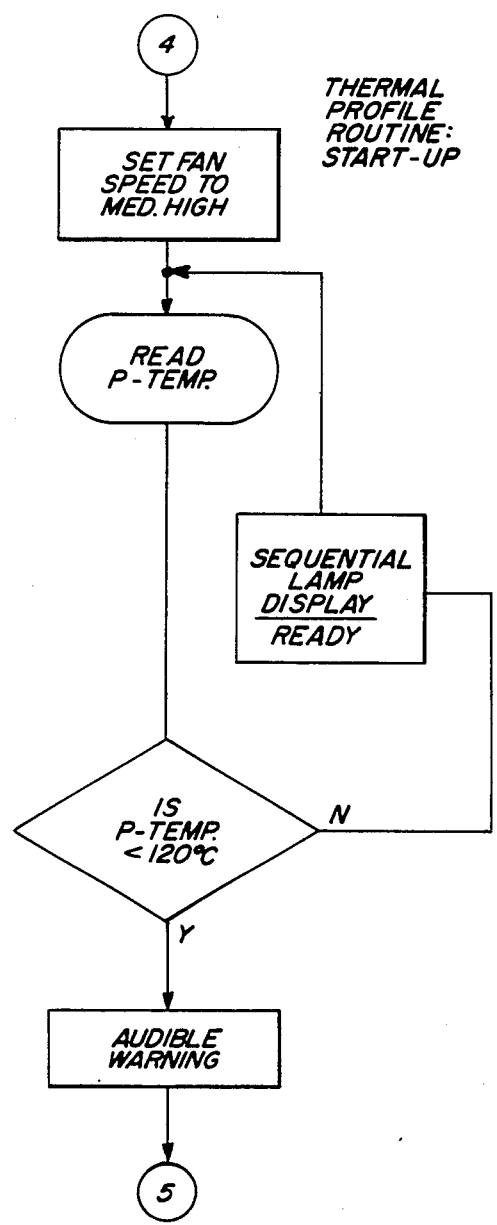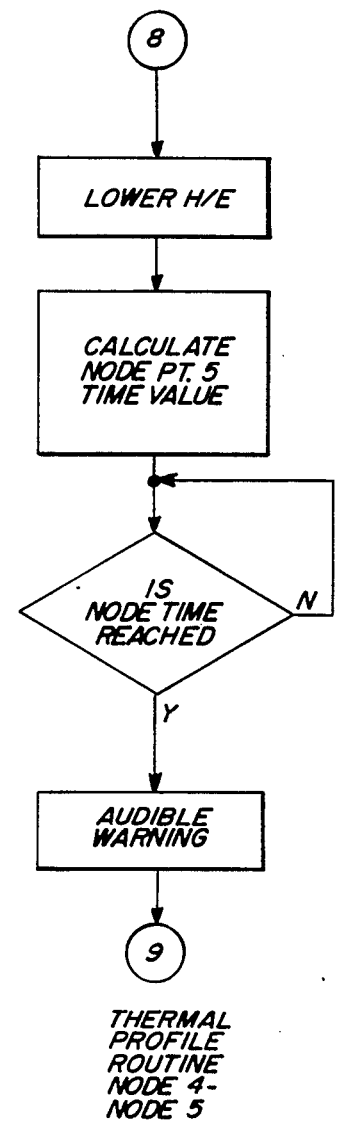
FIG. 6
FIG. 10

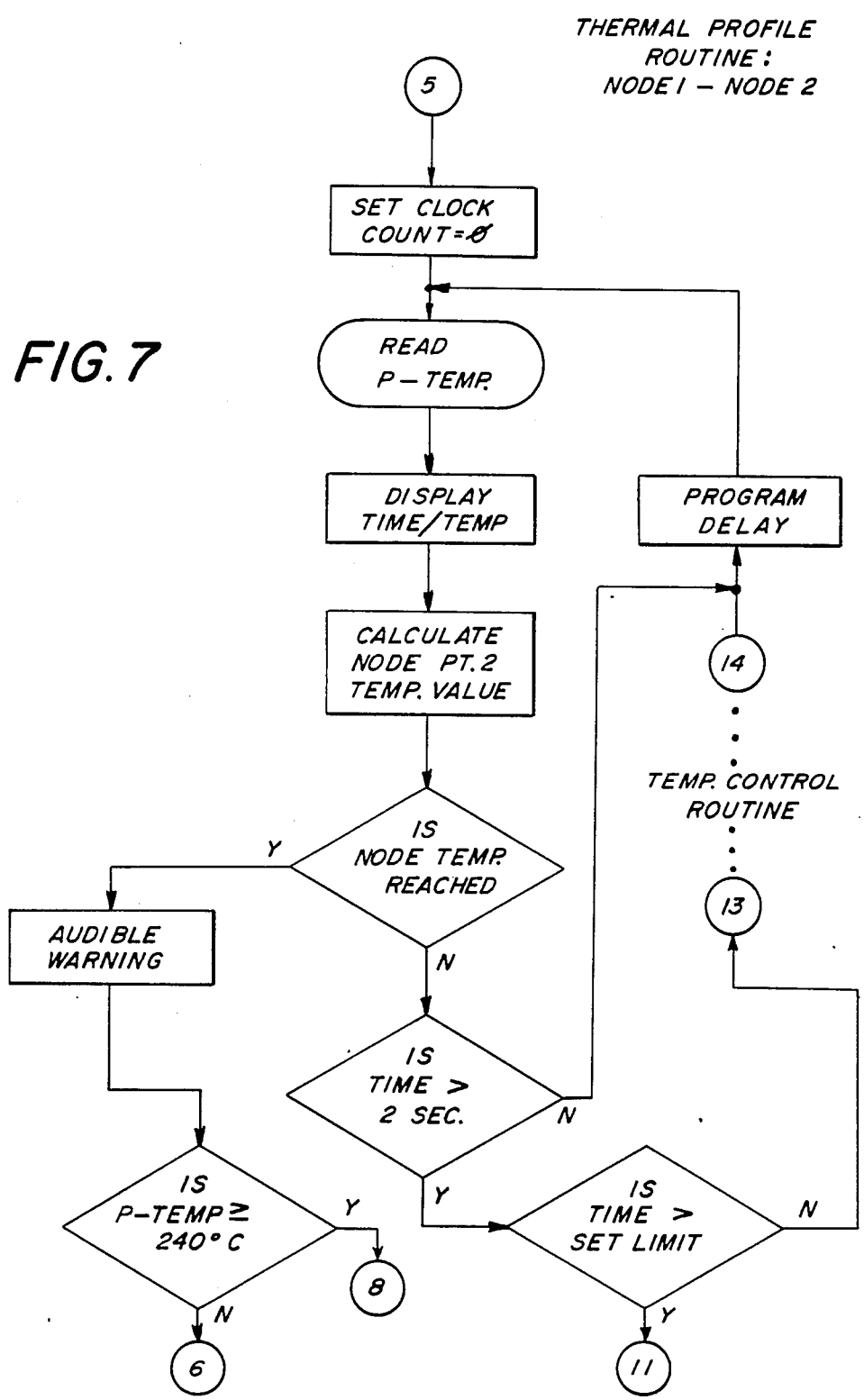

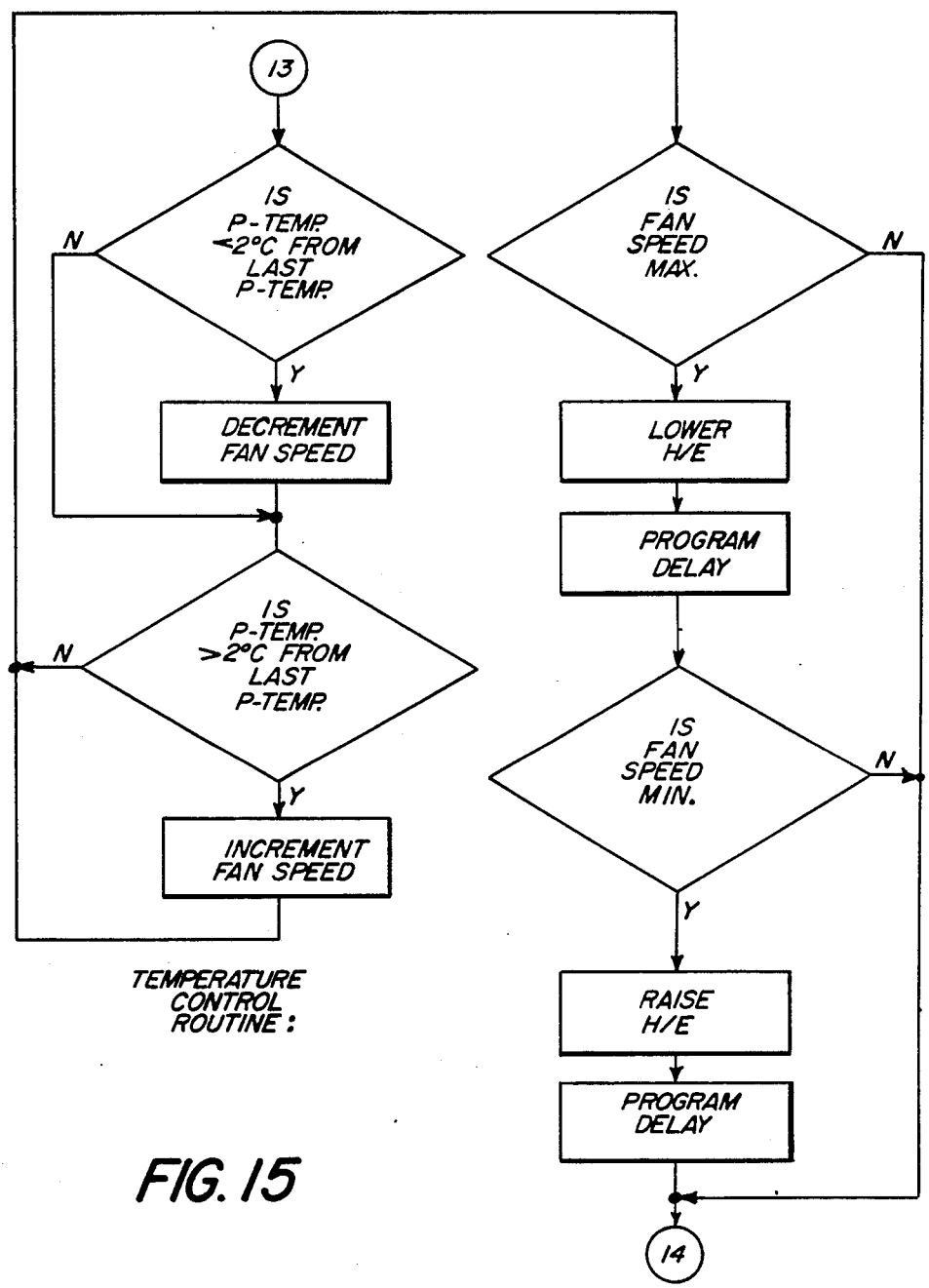

THERMAL PROFILE SYSTEM

BACKGROUND OF THE INVENTION

The present invention seeks to resolve the problem of accurately controlling a mechanized temperature/time dependent thermal process cycle. Presently existing equipment and processing techniques do not provide the user or the machine control mechanism with any information regarding what is happening to the materials to be thermally treated during a process cycle. Moreover, the suitable methods for thermal treatment presently used do not have known absolute control over material temperatures, but only approximate or relative control over such temperatures through the use of environmental feedback mechanisms.

It is, therefore, an object of the present invention to provide a closed loop environmental control system for thermally treating materials wherein such materials form an integral part of the feedback loop path to the control mechanism.

It is a further object of the present invention to be able to detect the mean temperature of the materials to be thermally treated during the process cycle and use that information to achieve absolute control over the thermal process cycle.

It is also an object of the present invention to provide several thermal profiles corresponding to different materials and temperature/time dependent processes to be selected by the user through the thermal process control mechanism.

Further objects will become evident hereinafter.

SUMMARY OF THE INVENTION

The apparauts of the present invention relates generally to the implementation of a characterized thermal profile upon a temperature/time dependent process. Specifically, the present invention provides an apparatus for controlling the thermal processing of any material susceptible to such processing in accordance with a closed loop environmental feedback system and a corresponding predetermined characterized thermal profile.

The apparatus for implementing a characterized thermal profile upon a temperature/time dependent process comprises a thermally transparent platform for supporting the material or materials to be thermally treated, a source of heat energy, a means for moving the source of heat energy either closer or farther away from the material or materials, a means for creating a controlled air flow through the platform to provide more gradual tempeature increases or decreases to the material or materials to be thermally treated, a temperature measuring means for detecting increases or decreases in the surface temperature of the material or materials, and a means for controlling the thermal treatment of the material or materials in accordance with a predetermined heating and cooling pattern.

The thermally transparent platform is preferred to be rectangular in shape and has a preselected locus or target area for the placement of the material or materials. The means for moving the source of heat energy includes a means for fixedly supporting the source of heat energy. The means for creating a controlled air flow through the platform is capable of being incrementally speeded up or slowed down in accordance with the required air flow.

The preferred temperature measuring means is an optical pyrometer, operating in the infra-red range, for measuring the emitted heat of the surface area of the material or materials to be thermally treated placed in the platform target area. The pyrometer is disposed at a distance of three to five inches from the material or materials with its detection element aligned within the range of 30 to 60 degrees from the upper surface of the material or materials. The pyrometer is preferred to be disposed at an angle of 45 degrees to the surface area.

The means for controlling the thermal treatment compares the detected temperature of the material or materials to be thermally treated in the target area to be predetermined pattern for causing the movement of the source of heat energy closer to or farther away from the material or materials and the increasing and decreasing of the flow of air in cooperation therewith to effectively achieve the required thermal treatment of the material or materials, all in accordance with the predetermined heating and cooling pattern.

BRIEF DESCRIPTION OF THE DRAWINGS

For the purposes of illustrating the invention, there are shown in the drawings forms which are presently preferred, it being understood, however, that the invention is not limited to the precise arrangements and instrumentalities shown.

FIG. 6 shows a flowchart of the Thermal Profile Routine: Start-up for the present invention.

FIG. 7 shows a flowchart of the Thermal Profile Routine: Node 1–Node 2 for the present invention.

FIG. 10 shows a flowchart of the Thermal Profile Routine: Node 4–Node 5 for the present invention.

FIG. 15 shows a flowchart of the Temperature Control Routine for the present invention.

DETAILED DESCRIPTION OF THE INVENTION

The following detailed description is of the best presently contemplated mode of carrying out the present invention. This description is not intended in a limiting sense, but is made solely for the purpose of illustrating the general principles of the invention.

Figure 1:
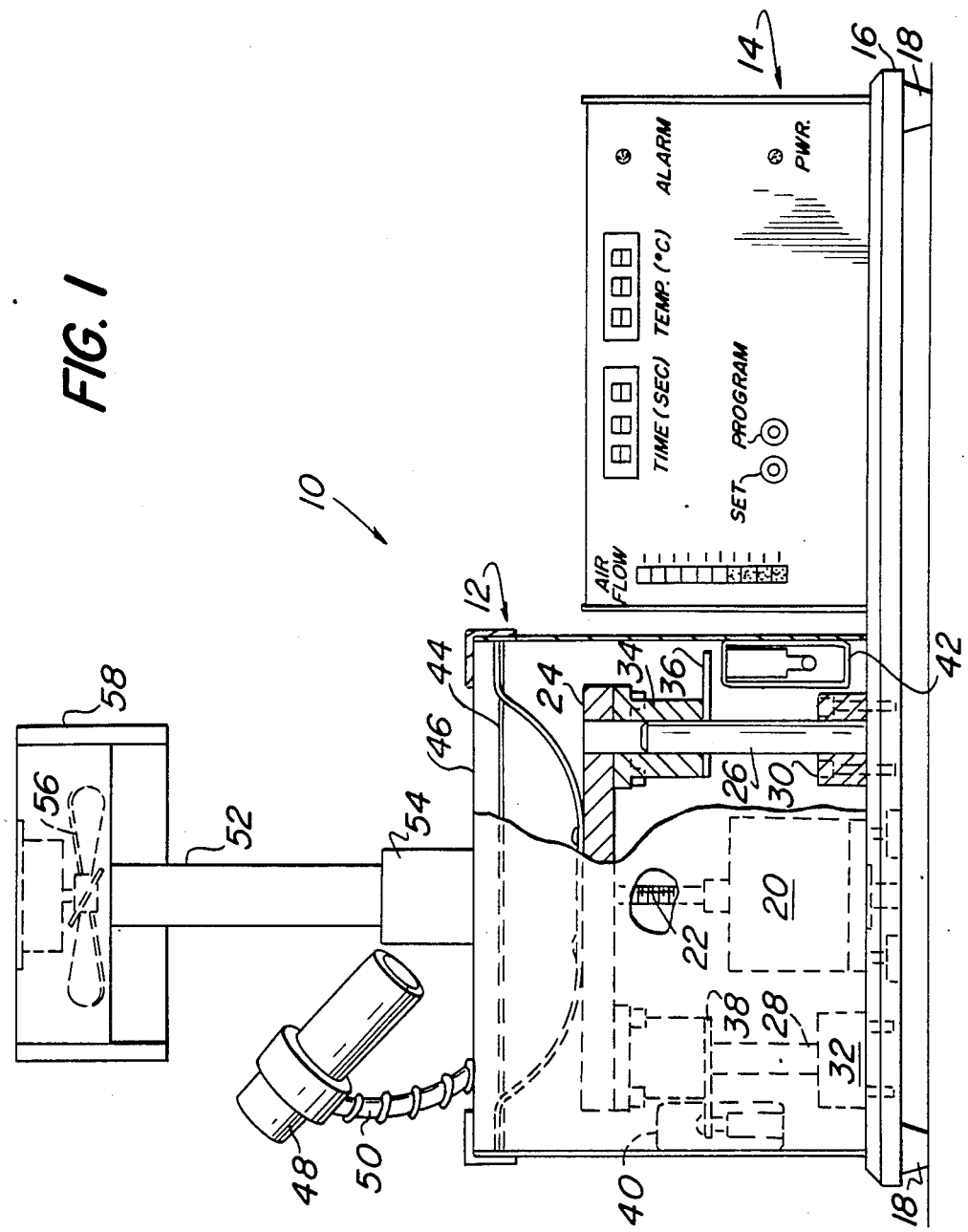
FIG. 1 is a front plan view, partially cut away, of the thermal profile system of the present invention showing the workstand and front plate of the controller.

Refering now to the drawings in detail, wherein like numerals indicate like elements, there is shown in FIG. 1 the thermal profile system of the present invention.

The thermal profile system 10 consists of a thermal treatment stand 12 and a control apparatus 14 disposed on a substantially rectangular mounting platform 16 having a supporting leg 18 located in each corner thereof. The legs 18 may be of plastic, firm rubber or other similar material capable of supporting the weight of the workstand 12, control 14 and mounting platform 16. The legs 18 may also be adjustable to vertically alter the height, at that leg, of the mounting platform 16 so as to provide a capability for leveling the workstand 12.

The workstand 12 is comprised of several interrelated operating parts. The base portion of the workstand 12 houses a reversible motor 20 mounted to the platform 16 having a threaded shaft 22 extending vertically upward and connected to an elevator platform 24. The elevator platform 24 is guidingly engaged with two vertically oriented shafts 26, 28. The shafts 26, 28 are fixedly mounted to the platform 16 by screws threaded through the platform into identical collars 30, 32 supporting the lower ends of the shafts 26, 28. The collars 30, 32 serve as the means for maintaining the shafts 26, 28 in substantially a vertical orientation.

The upper ends of the shafts 26, 28 are free standing and aligned to facilitate the cooperative up-and-down movement of guide means 34 of the elevator platform 24 thereupon. Attached to the underside of the guide means 34 are indicator arms 36, 38 which contact, respectively, upper and lower limit switches 40, 42. The limit switches 40, 42 serve to stop the motor 20 when the elevator platform 24 reaches its maximum or minimum height.

The motor 20, the elevator platform 24 motion mechanism, is an AC reversible motor which generates motion on a linear axis. As can be seen from the drawing, the motor 20 is mounted in such a manner as to impart motion in a vertical direction, up or down. Line voltage, 120 VAC, is applied to the appropriate motor winding by way of relay contacts controlled by digital select lines from the control box 14 to be described more fully hereinafter.

Mounted on the upper surface of the elevator platform 24 by any suitable means capable of withstanding high temperatures without loss of material integrity, i.e. stainless steel screws, is a heating element 44. The heating element 44 is preferred to be of an electrical type for uniform dispersion of heat energy. The heating element 44 is powered by an RMS voltage regulator to guarantee substantially constant energy emission over varying line voltages. The elevator platform 24 upon which the heating element 44 is mounted moves up or down to create varying air gap distances between the material to be thermally treated and the source of heat energy. The air gap allows various diffusion levels of the heat energy transfer medium, primarily convection currents in the air. This effect can be further enhanced by the increase or decrease of the flow of air around the workpiece.

At its maximum height the heating element 44 almost contacts a material treatment platform 46 which is supported along each of its edges by the housing walls. The material treatment platform 46 consists of a thermally transparent material capable of resisting deformation and loss of material integrity in high temperature enviroments. One of the better suited materials is large mesh thermally conductive metallic screening.

Located in the upper left quadrant of the treatment platform 46, when viewed from above, is a target area alignment means having arms of equal length extending perpendicularly outward from a vertex along the platform surface. The alignment means is configured so that one corner of a rectangularly shaped workpiece may be placed easily within its opening to properly align the workpiece on the treatment platform 46. An alternate alignment for when the workpiece has one substantially longer dimension is to position the workpiece against the alignment means at the ends farthest from the vertex. The ends of the alignment means have been formed at an angle of 45 degrees to the perpendicular angle the arms form with each other at the vertex of the alignment means. The 45 degree angle formed edges are in linear alignment with each other so that one side of a workpiece may be positioned against them easily and accurately. The alignment means is positioned so that a 4×4 inch workpiece can be aligned over the center portion of the treatment platform 46 but may be made to adjustably move closer to the edges of the platform to allow for larger dimensioned workpieces.

Located above the upper left quadrant of the treatment platform 46, when viewed from above, is a pyrometer 48 fixedly mounted to a stationary arm 50 extending upward from the level of the platform. The arm 50 holds the pyrometer in a fixed relationship to the treatment platform 46 in order to be able to accurately measure temperatures of workpieces in the target area of the platform. The pyrometer 48 preferred to be an optical temperature sensor in the infra-red range. The pyrometer 48 provides a non-contacting measurement device for optically sensing the average surface temperature of the workpiece by outputting a DC voltage which is proportional to the detected temperature. The output signal [DC voltage] is proportioned so that 1 mv.=1° C. ; e.g. 100 millivolts is equivalent to 100° C.

Viewing the thermal profile system from the front, as in FIG. 1, at the rear of the treatment platform 46 a support member 52 having a base 54 is attached for supporting above the treatment platform 46 an airflow circulating means 56. The airflow circulating means or fan 56 is disposed in a tube-like housing 58 substantially above the center of the treatment platform 46 and the heating element 44, elevator platform 24 and motor 20, which are centrally located within the housing, to artifically induce air movement to control the heating and cooling process of the workpiece, as is necessary. The fan 56 is a brushless DC type assembly having a relative air flow or fan speed proportional to its control voltage. Its placement is such as to enhance the flow of air above and around the workpiece.

The control box 14 is electrically connected to the devices located on the workstand 12 by a cable (not shown) so that effective control over the thermal process can be maintained at all times. The control box 14 provides both visual and audible indications of the process stages and device status. An Airflow Monitor made from a group of sequentially energized lamps indicates the status of the fan 56. The elapsed time [TIME] and workpiece temperature [TEMP] are displayed on separate groups of light emitting diodes. TIME is indicated in seconds and TEMP is indicated in degrees C. A power-on indicator lamp is provided to show when power is applied to the system. SET and PROGRAM switches, which will be described more fully hereinafter, are provided for setting and modifying the control parameters of the present invention. An audible warning or alarm is provided for sounding an alarm to indicate status or fault when the system is left temperarily unattended. A visual warning device is also provided in the form of a colored lamp forming part of the alarm circuit.

Figure 2:
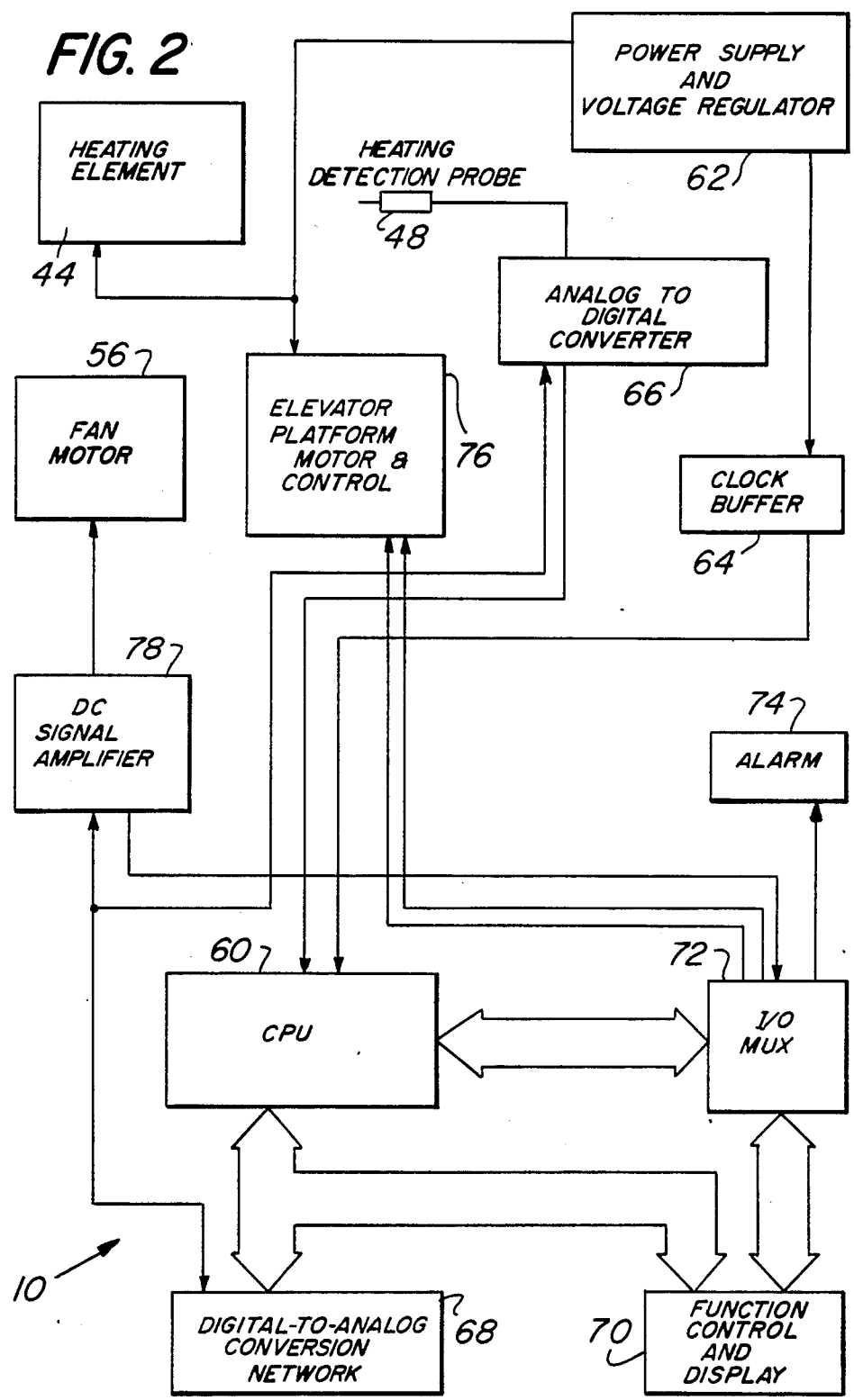
FIG. 2 is a block diagram of the thermal profile system of the present invention.
Figure 3:
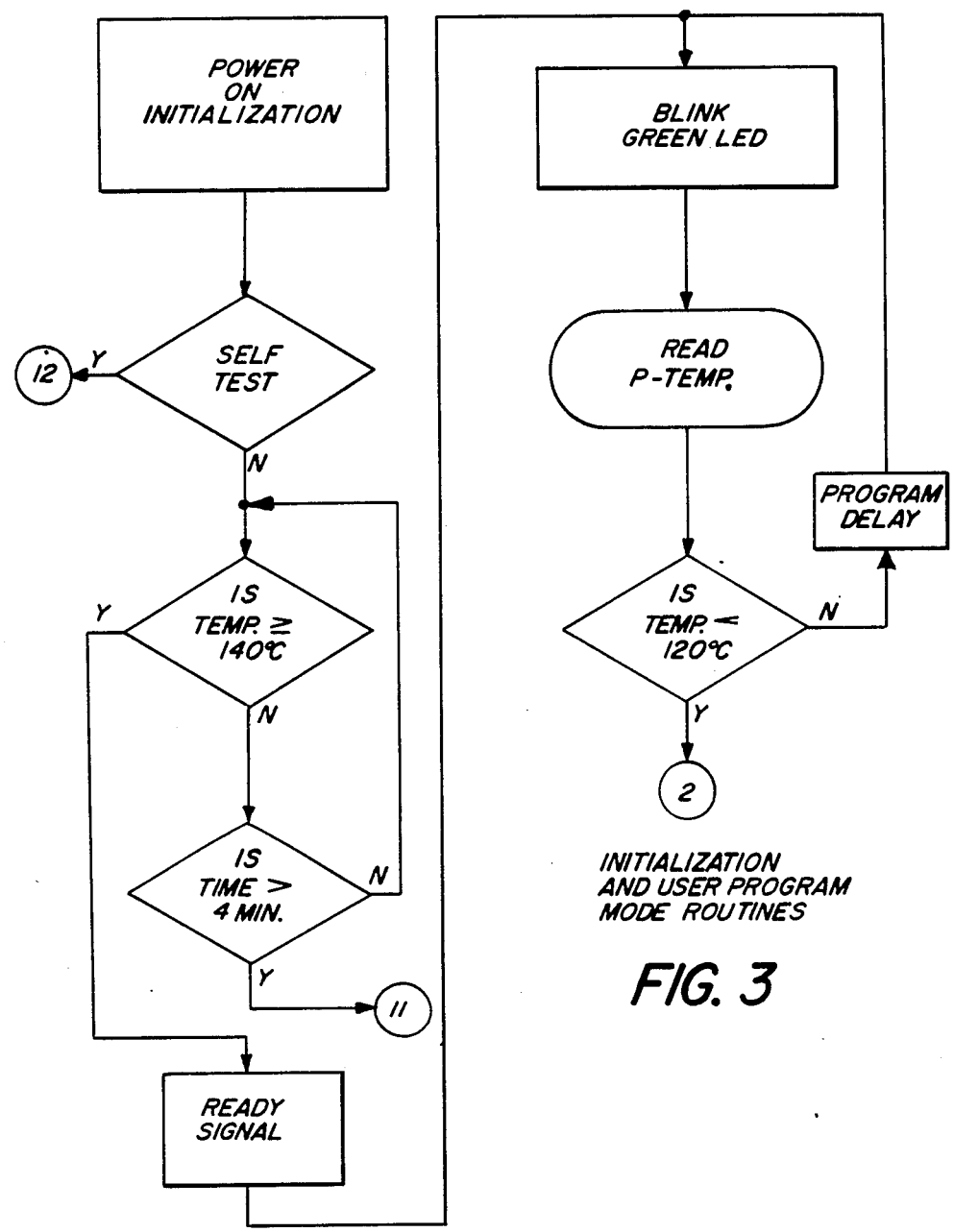
FIG. 3 shows a flowchart of the Initialization and User Program Mode Routines for the present invention.
Figure 4:
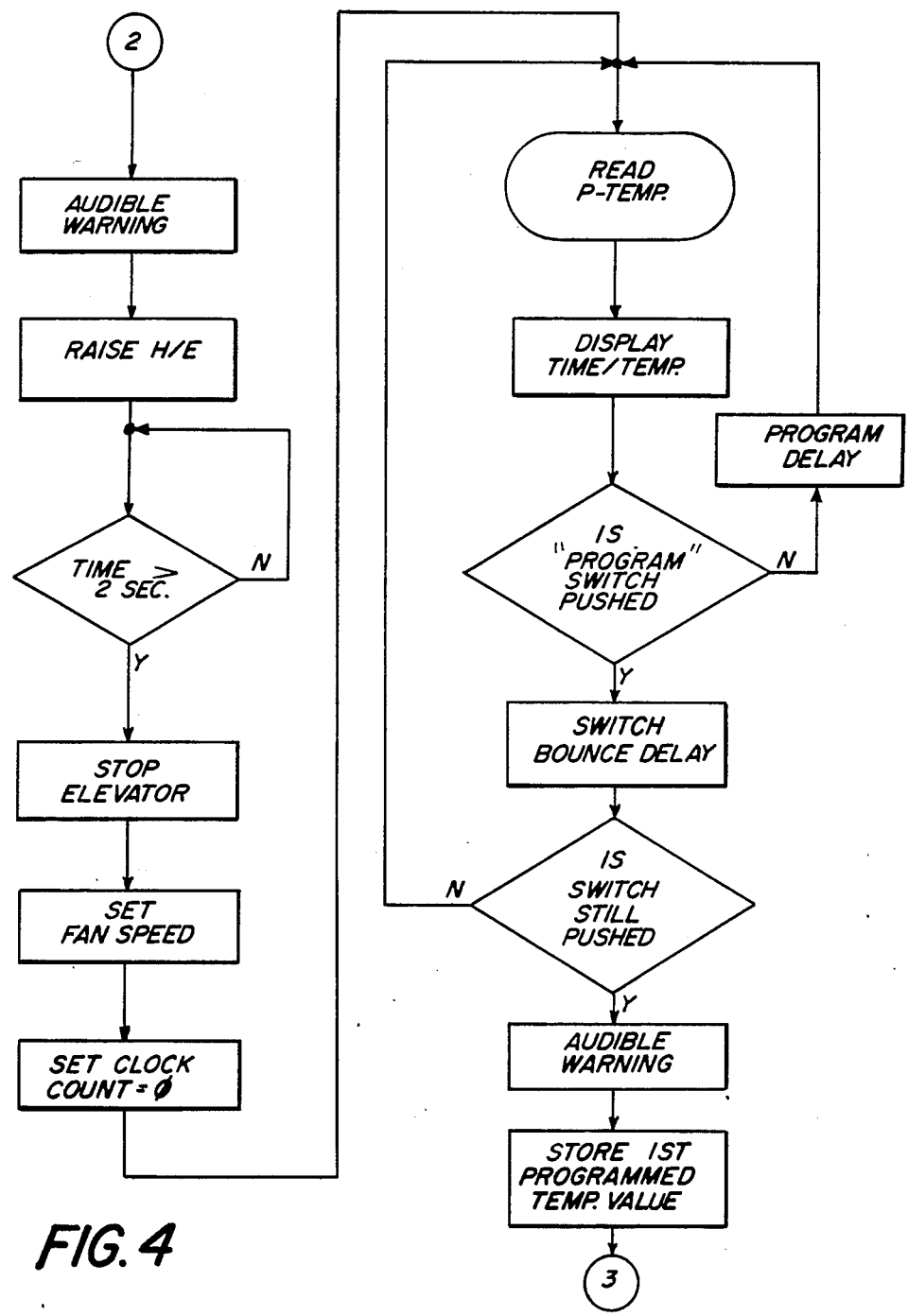
FIG. 4 shows a flowchart of the continuation of the User Program Mode Routine for the present invention.
Figure 5:
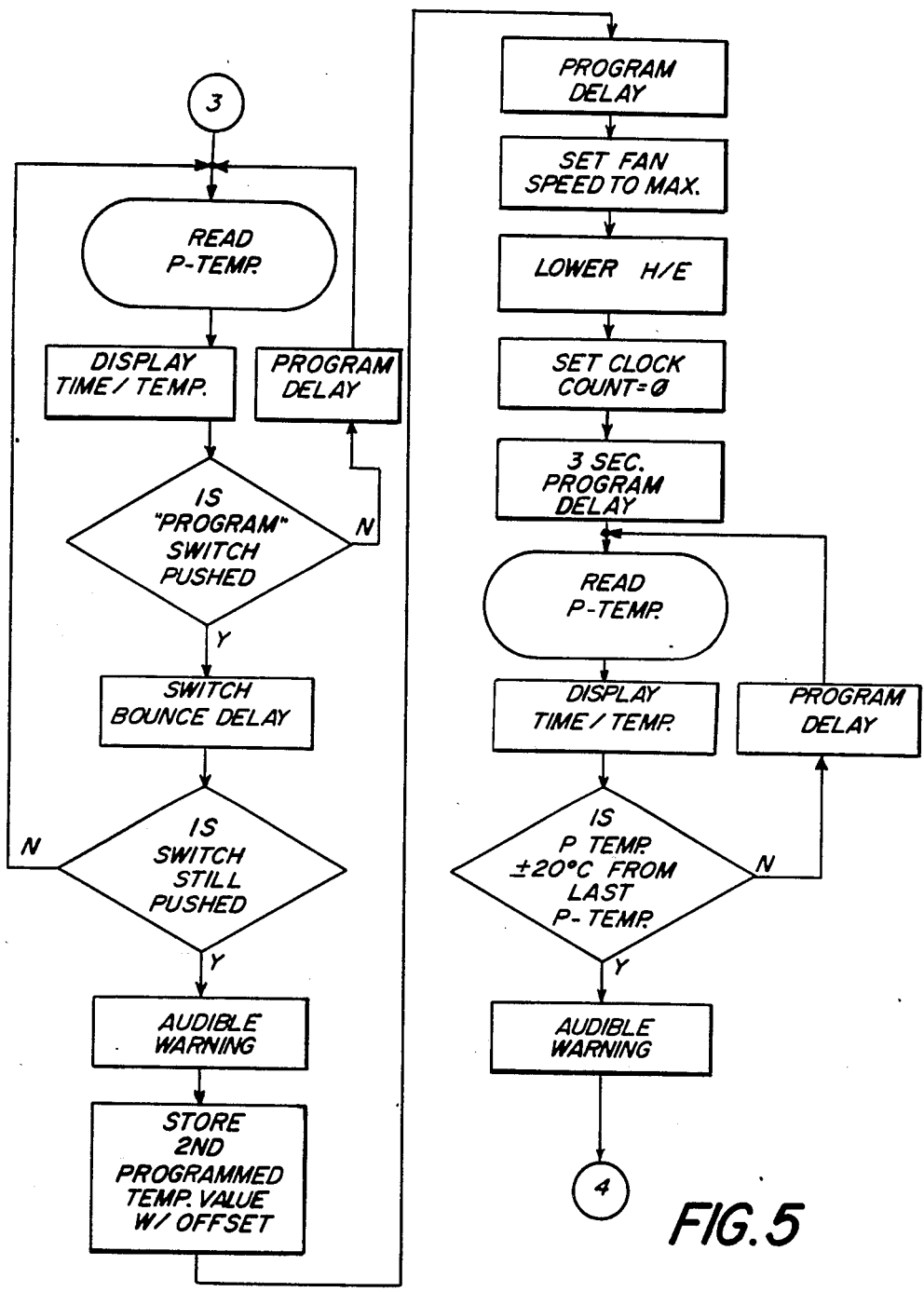
FIG. 5 shows a flowchart of the continuation of the User Program Mode Routine for the present invention.

Referring now to FIG. 2 there is shown a block diagram of the electrical connections among the several elements of the present invention. The overall control for the entire system resides in the central processing unit or CPU 60. The CPU 60 is comprised of several standard devices; a micro-processor, an I/O management device with on-board random access memory and a read-only memory. The micro-processor may be any of several suitable devices presently available from a variety of manufacturers but, due to the nature of the environment and its necessary control characteristics, the 8-bit Rockwell 6502 micro-computer is preferred. Associated with the micro-computer is a peripheral I/O management device with 16 control/data lines, i.e. Rockwell 6532. This device also has available 125 Bytes of RAM, random access memory, which is used for operating system variables. Also a part of the CPU 60 is a 2K-Byte EPROM containing the operating system and the predetermined thermal profile for the particular material to be thermally treated. The EPROM, or erasable programmable read only memory, can be any standard 8-bit memory device, i.e. AMD 2716. The EPROM can be removed and replaced by other EPROM's having different thermal profiles for other materials. Alternatively, several EPROM's can be provided with only one of the group being selectable at a time through external programming of the system which will be more fully described hereinafter.

The CPU 60, as well as all the electrical devices which have been or will be described, is connected to and has its power supplied by a power supply and voltage regulator 62. Line voltage [120 VAC] is applied to the input of the power supply and converted to the voltages required by the devices, +5 VDC and +14 VDC. The power supply 62 also provides 120 VAC to the motor 20 and the heating element 44.

To provide a counting capability for the CPU 60 the clock buffer 64 uses the 60 Hz recurrence of the AC voltage from the power supply transformer as applied to the DC voltage rectifier. The voltage, which occurs once every 1/60 of a second at the tap point, is amplified and applied to the timing control input of the micro-processor to provide a stable clock count. The count is used in the control of the system and providing the TIME function display when required.

The CPU 60 monitors and regulates the flow of information and control signals throughout the system. In describing this continuing task, I will start with the heat detection probe or pyrometer 48. This device continually monitors the average surface temperature of the workpiece when the system is powered. As mentioned above, the pyrometer 48 is located above and to the left rear of the thermal treatment platform 46 when viewing the system from the front. Although the ideal position for the pyrometer 48 would be to position it directly over the center portion of the heating element 44 and the treatment platform 46, this would be detrimental to the pyrometer 48. The exposure to direct heat from the heating element 44 either from around the edges of the workpiece or directly if no workpiece were on the platform 46 would distort an accurate temperature measurement. Knowing, of course, that any angle at which the pyrometer would be disposed would affect the reflected heat measurement from the surface of the workpiece, a 45 degree angle from the surface of the treatment platform 46 was chosen as the optimum position. This angle was chosen because the target area, the surface area of the workpiece, would increase with an increasing divergent angle of orientation from the selected angle reducing the accuracy of the temperature measurement. The pyrometer 48 is disposed approximately 3-5 inches above the target area.

Two leads are connected from the pyrometer 48 to the analog-to-digital converter 66 which amplifies and correlates the voltage signals optically created by the pyrometer 48 reading the emitted infra-red heat energy from the surface area of the workpiece. The CPU 60 requests the temperature reading by applying a signal to the analog-to-digital convertor 66 [device selection signal] for the resulting signal to be applied to a resistor ladder network in the digital-to-analog conversion network 68. The digital-to-analog conversion network 68 consists of the resistor ladder network and a buffer for voltage level adjustment between the voltage level acceptable to the micro-processor and that required by other devices in the system. Both the resistor ladder network and the buffer are integrated circuit devices readily available from a variety of manufacturers.

The proportional voltage signal originating from the pyrometer 48 is passed through a voltage comparator/amplifier in the analog-to-digital convertor 66. The buffered signal from the pyrometer 48 is compared to a DC voltage generated by the resistor ladder network which originated as a binary number generated by the micro-processor. The compared signal is level adjusted in the voltage level buffer and presented to the micro-processor on its data bus.

To make a temperature measurement the micro-processor generates incrementally larger numbers to the resistor ladder network which, in turn, generates a corresponding increasing DC voltage in 19.5 mv. increments. When the generated voltage becomes greater than the buffered signal from the pyrometer 48, the output of the comparator/amplifier will switch from a high to a low state. The output signal from the comparator/amplifier is buffered by a switching transistor. The transistor acts as a signal inverter and a voltage level translation device between the higher voltage of the comparator/amplifier and the lower voltage of the micro-processor. The change in state of the output signal is interpreted by the micro-processor as the completion of an analog-to-digital cycle. Upon completion of such cycle, the micro-processor takes the last number loaded into the resistor ladder network and decrements this value by one which is indicative of the value of the input signal of the pyrometer 48. [1 count in binary=1 mv.×(19.5)=1° C.]. To display the detected temperature value the micro-processor outputs a binary word directed to the function control and display 70 on its data bus.

In order to direct the data to the appropriate location the micro-processor outputs a device selection signal or code to the I/O multiplexer 72. The I/O multiplexer 72 is comprised of a standard 4-bit binary-to-decimal convertor which allows a binary number of 4-bit length to select one of ten designated outputs dedicated to a single function. There are also several signal lines which are independent of the convertor. The device selection code is interpreted by the multiplexer 72 to cause the appropriate LED display to accept each assigned character of the temperature data being transferred from the micro-processor into the corresponding position of the display. Similarly, the time data is sent from the micro-processor to the appropriate LED display by sending the data for the character to be displayed directly to the LED display with the device selection code to be passed on by the multiplexer 72.

Each of the LED devices display numeric characters and are available from various manufacturers. For the system of the present invention the LED displays will each display three characters at a time. Associated with each of the LED displays are buffer drivers which are also standard devices. A blanking control is provided which automatically turns the display off to conserve power. The LED displays are also used as a warning device for the operator in addition to the alarm 74.

The alarm 74 is controlled by the micro-processor through a device selection code and provides both an audible "beep" and a blinking lamp as a warning or an indication of the completion of a step in the process. Both warning or indication devices will be described more fully hereinafter.

The CPU 60 also receives control signals from the control box 14 from the SET and PROGRAM switches. The switches are connected directly to the CPU 60 and by-pass the BCD convertor. The function of these switches will be explained below.

The CPU 60 outputs appropriate control signals to the various devices housed on the workstand 12. Through the I/O multiplexer 72 signals can be sent to the elevator platform motor control 76 to operate the motor 20 and elevator platform 24 in either the up or down direction. Each of these signals is digital and is buffered by transistors in order to actuate the motor relays. This, of course, will either raise or lower the heating element 44 providing more or less heat energy to the workpiece. Separate and distinct device selection codes are used for the "raise" command and the "lower" command. Each of the commands can be cancelled by the elevator platform 24 contacting either the upper or lower limit switches 40, 42 which will halt the movement of the elevator platform 24 instantly.

The fan motor 56 is controlled by a DC signal amplifier 78 which is connected to the digital-to-analog conversion network 68. The control or signal voltage for the amplifier 78 is generated by the resister ladder network from a binary number loaded into it by the microprocessor. The number representing the desired fan speed is converted to a voltage level and applied to the DC signal amplifier 78. The DC signal amplifier 78 provides a controlled DC voltage to the fan motor 56 and, at the same time, provides a signal to the airflow monitor. The value of the voltage signal applied to the airflow monitor controls the number of sequential lamps which light. The greater the value, the more lamps which become energized. As the value decreases, fewer lamps are energized. The airflow monitor lamps follow the fan speed exactly. The signal for the airflow monitor is another of the direct signals which passes through the I/O multiplexer 72.

Figures 13, 14:
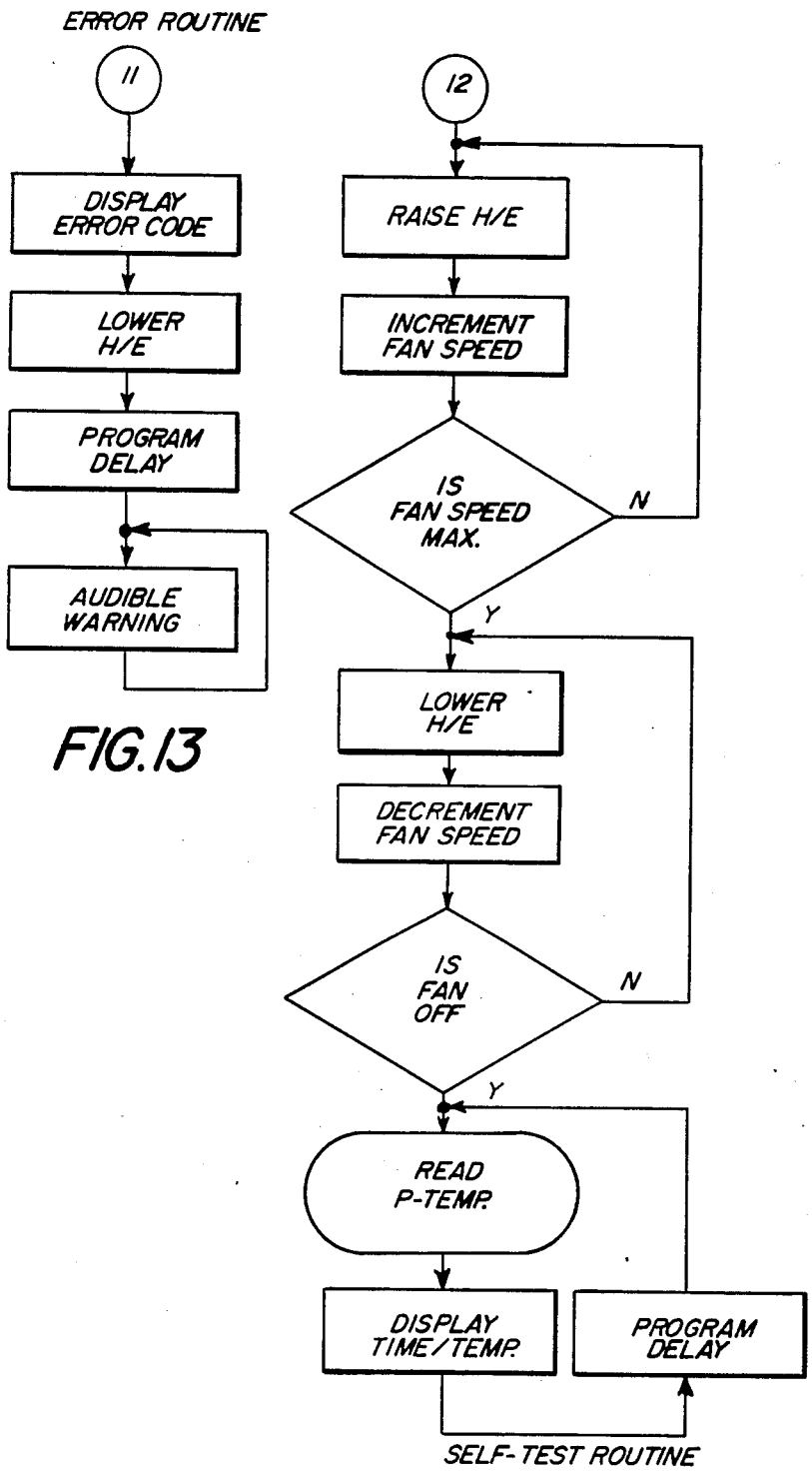
FIG. 13 shows a flowchart of the Error Routine for the present invention.
FIG. 14 shows a flowchart of the Self-Test Routine for the present invention.

For the ease of understanding the control program of the present invention, SN62 solder paste will be referred to as the material which is thermally treated. However, the invention should not be construed to be limited to the one material. Referring now to FIGS. 3 through 15, flowcharts of the program control are shown of the present invention. In order to initiate the program the power switch for the system must be turned on. Initialization of the system includes sampling positions and status of the various elements and devices. When complete a Self-Test or diagnostic routine can be requested. Reference can be made to FIG. 14 for the Self-Test Routine. The diagnostics include the raising of the elevator platform 24 and heating element 44 and incrementing the speed of the fan 56 from off to maximum. This is followed by the lowering of the elevator platform 24 and heating element 44 and the decrementing of the speed of the fan 56 from maximum to off. Once the heating and cooling devices are checked the temperature measurement and function display devices are exercised to test their functionality. The temperature of the target area of the treatment platform 46 is read and displayed, as is the elapsed time for accomplishing the test. The fan speed was displayed as the fan 56 was being exercised from off to maximum to off. The diagnostics routine will continue to repeat until the power is turned off and then on again, reinitializing the system.

To complete the initialization routine the temperature of the target area is measured to determine whether it has reached approximately 140° C. The program permits a four minute delay before a fault is determined. This allows the operating temperature of the present invention to be reached and allows the operator/user to place the sample or test workpiece on the platform 46. If a fault is determined the program jumps to an error routine to be described below.

Once the target area temperature has reached 140° C. the system advises the operator by giving off an audible signal and blinking the indicator lamp. The User Program Mode is begun by reading the temperature detected by the pyrometer 48, P-TEMP, and checking to see whether the average emitted heat from the surface area of the test workpiece is greater than 120° C. If the temperature has not reached that point the system pauses for a short delay before checking again. Once the temperature is reached an audible warning is sounded and the heating element 44 and elevator platform 24 are raised for a time period of two seconds. The fan 56 is now set to its minimum speed and the clock is reset to zero. P-TEMP is read again and the TIME and TEMP values are displayed. An inquiry is begun to determine whether the PROGRAM switch is pushed with delays for renewed inquiry and de-bouncing of the switch. If the PROGRAM switch is held in an audible warning sounds and the first programmed temperature value is stored in memory. The PROGRAM switch is to be actuated when the first sign of thermal state change is visually detected in the material by the operator/user.

Referring now to FIG. 5, P-TEMP is read again and the TIME and TEMP values are displayed. A second inquiry is made to determine if the PROGRAM switch is pushed with the same delays and testing for continued depression of the switch. If the PROGRAM switch is detected as being pushed an audible warning is sounded and the second programmed temperature value with an offset is stored in memory. The PROGRAM switch is actuated the second time when a complete thermal state change of the material on the test workpiece has been visually detected by the operator/user.

A longer program delay now occurs follwed by several device commands to cool down the test workpiece. The speed of the fan 56 is set to its maximum, the heating element 44 and elevator platform 24 are lowered and the clock is reset to zero. The status of this short cool down period is monitored by reading the P-TEMP, displaying the TEMP and TIME values and repeating those steps until the detected P-TEMP is 20° C. from the last reading. The test is performed to determine when the test workpiece can be removed. An audible warning is sounded announcing the end of the Program Mode. The system is ready for implementing the Thermal Profile Routine.

Unless otherwise instructed the system will begin the Thermal Profile Routine: Start-up procedure. Referring now to FIG. 6, the fan 56 will be set to a medium high speed and the p-TEMP will be read. The detected P-TEMP will be checked to see whether it is greater than 120° C. The test is performed to determine when a workpiece is placed on the treatment platform 46. A sequential lamp display, a blinking of all the lamps in a predetermined sequence indicates the beginning of the thermal process. When the workpiece is in place and the P-TEMP greater than 120° C. an audible warning sounds indicating the completion of the Start-up procedure.

The Thermal Profile Routine continues, as shown in FIG. 7, by stepping through the characteristic profile beginning with NODE 1–NODE 2. The clock is reset to zero and the P-TEMP is read displaying the TIME and TEMP values. NODE 2 temperature value is calculated and an inquiry is initiated whether the Node 2 temperature has been reached. If the Node 2 temperature is reached an audible warning is sounded and a test is performed to determine whether the workpiece temperature is greater than 240° C. If the P-TEMP is greater than 240° C. then the program jumps to the NODE 4–NODE 5 step which will be explained below. If the P-TEMP has not reached 240° C. then the process continues with the NODE 2–NODE 3 step.

If the Node 2 temperature is not reached when tested then a delay not to exceed two seconds is begun to determine whether the P-TEMP has reached Node 2 temperature. If the time period is exceeded a test of whether the time which has been counted is greater then a Set Limit. If greater than the Set Limit the program jumps to the Error Routine. If the Set Limit has not been reached then the Temperature Control Routine is begun.

The Temperature Control Routine, FIG. 15, monitors smaller increments of temperature in order to more accurately regulate the speed of the fan 56 and the height of the heating element 44 and elevator platform 24. P-TEMP is read and a determination is made whether there is a 2° C. difference from the last reading. If P-TEMP is less than 2° C. from the last P-TEMP reading the fan speed is decremented. If P-TEMP is greater than 2° C. from the last P-TEMP reading the fan speed is incremented. The fan speed is then tested to see whether it has reached its maximum. If the maximum fan speed has not been reached the program returns to the Node 2 temperature test step. If the maximum fan speed is reached the heating element 44 and elevator platform 24 are lowered with an accompanying delay for the devices to respond. The fan 56 is then tested to see whether its minimum speed has been reached. If the fan 56 has not reached its minimum speed the program returns to the Node 2 temperature test step. If the fan 56 has reached its minimum speed the heating element 44 and elevator platform 24 are raised with an accompanying delay for the devices to respond. After completion of one pass of the Temperature Control Routine the program returns to the Node 2 temperature test step as shown in FIG. 7. The Temperature Control Routine may be repeated as many times as is necessary or until the Set Limit is reached.

Figure 8:
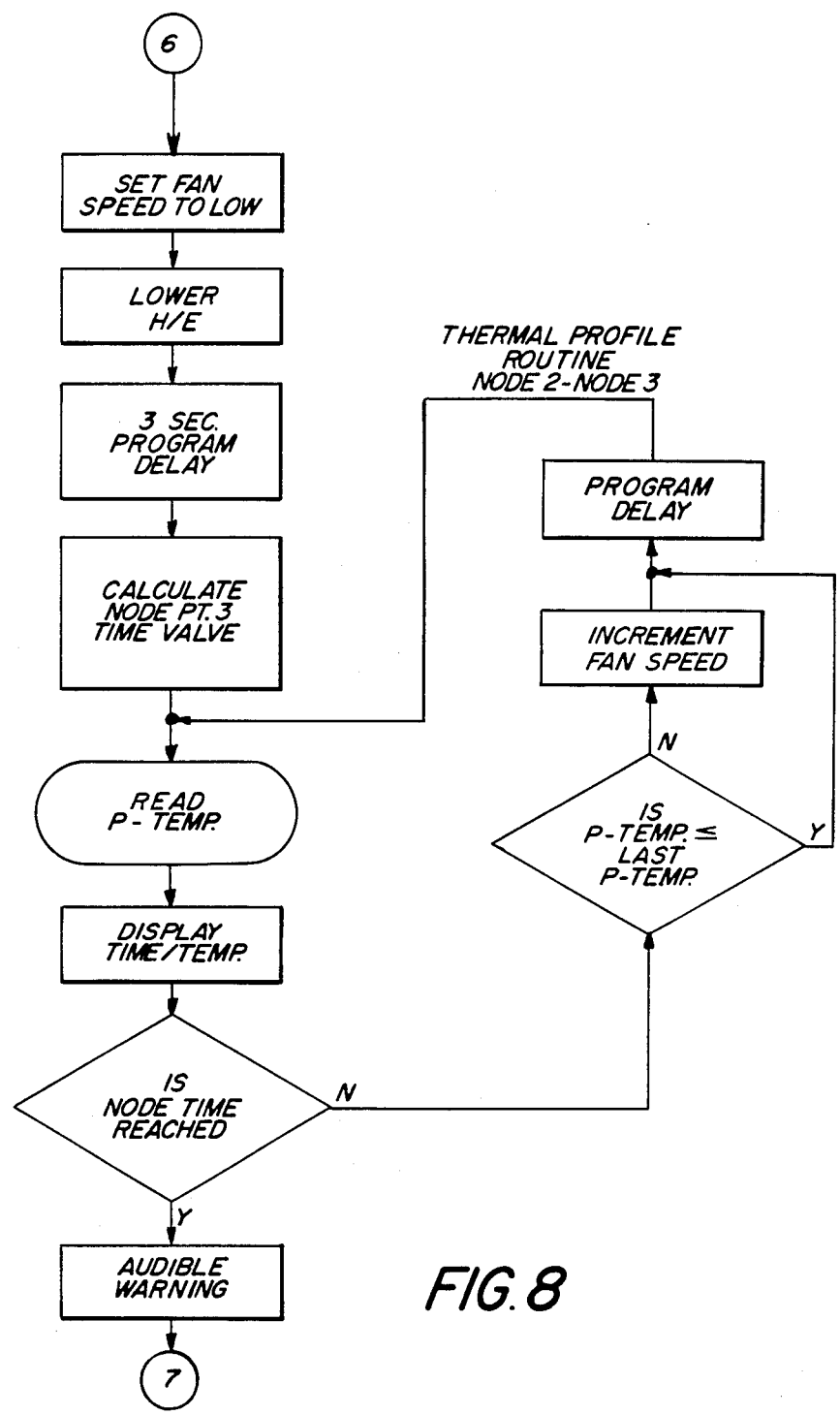
FIG. 8 shows a flowchart of the Thermal Profile Routine: Node 2–Node 3 for the present invention.

Continuing with the Thermal Profile Routine, the next step NODE 2–NODE 3, as shown in FIG. 8 for holding a predetermined temperature for a defined time interval, is now performed. The fan speed is set to low and the elevator platform 24 and the heating element 44 are lowered followed by a three second delay to accomplish the commands. The Node 3 time value is calculated and the current P-TEMP is read and both TIME and TEMP are displayed. A test to determine whether the Node 3 time has been reached is initiated. If the Node 3 time has not been reached the P-TEMP is checked to determine whether it is less than or equal to the last P-TEMP reading. If it is the Node 3 time test is repeated. If the current P-TEMP is greater than the last P-TEMP reading then the speed of the fan 56 is incremented and then the Node 3 time test is repeated. If the Node 3 time has been reached an audible warning is sounded and the process goes on to the next step.

Figure 9:
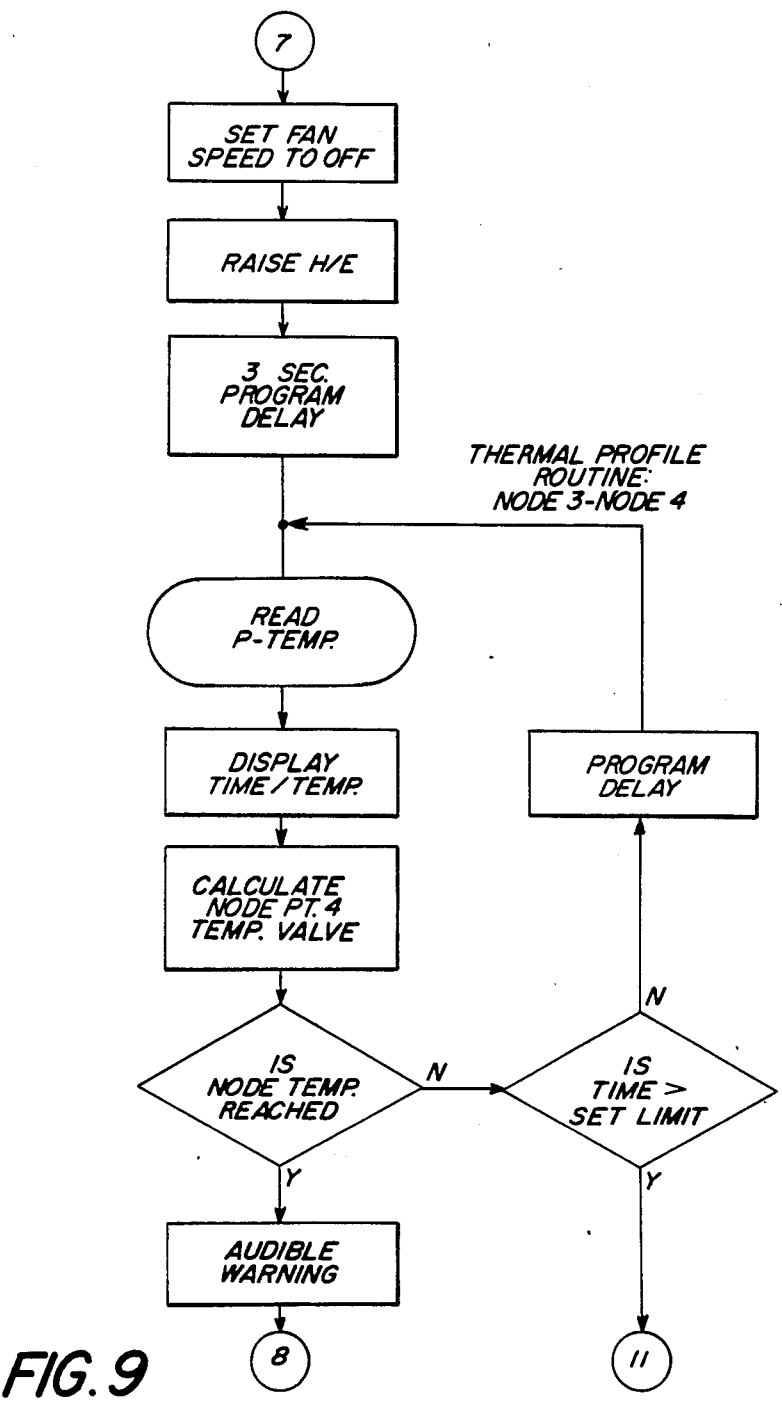
FIG. 9 shows a flowchart of the Thermal Profile Routine: Node 3–Node 4 for the present invention.

The next step in the Thermal Profile Routine is the NODE 3–NODE 4 step as shown in FIG. 9. This step is a transition step allowing the temperature to increase to the next nodal point value above the profile temperature. The fan 56 is set to off and the elevator platform 24 and the heating element 44 are raised followed by a three second delay to accomplish the commands. The P-TEMP is read and the TIME and TEMP values are displayed. This is followed by the calculation of the Node 4 temperature value. A test is initiated to determine whether the Node 4 temperature has been reached. If the temperature has not been reached a check to whether the Set Limit has been exceeded is undergone. If the Set Limit is exceeded the program jumps to the Error Routine. If the Set Limit has not been exceeded then the Node 4 temperature test is repeated. When the Node 4 temperature is reached an audible warning sounds and the process goes on to the next step.

The NODE 4–NODE 5 step of the Thermal Profile Routine, FIG. 10, is designed to maintain the temperature for a defined time interval. The step begins with the lowering of the elevator platform 24 and heating element 44 and continues with the calculation of the Node 5 time value. A test is initiated to determine whether the Node 5 time value has been reached. If it has not been reached then the test is repeated. When the Node 5 time is reached an audible warning sounds and the process goes on to the next step.

Figures 11, 12:
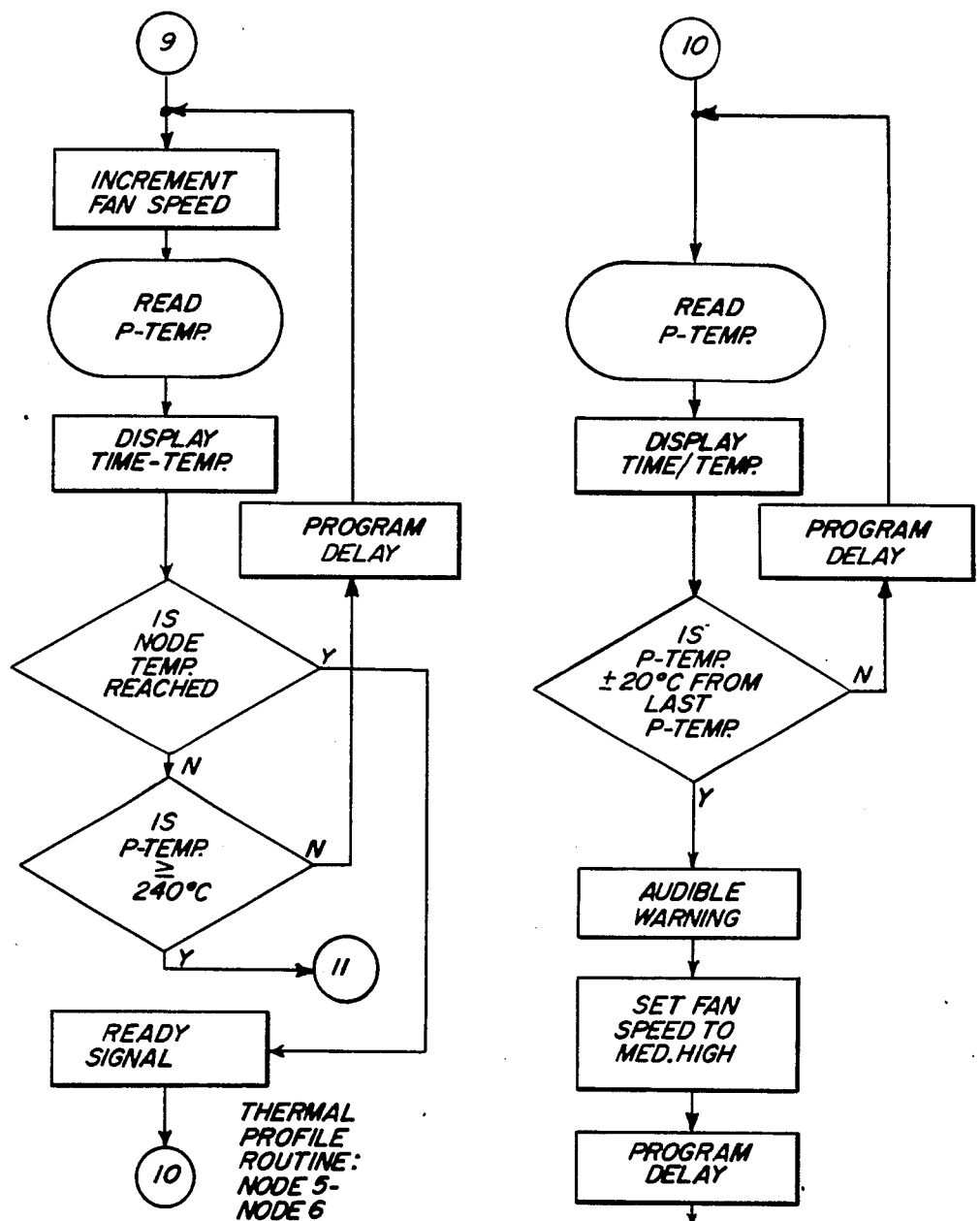
FIG. 11 shows a flowchart of the Thermal Profile Routine: Node 5–Node 6 for the present invention.
FIG. 12 shows a flowchart of the Thermal Profile Routine: Cool Down for the present invention.

The process continues, as shown in FIG. 11, with the NODE 5–NODE 6 step of the Thermal Profile Routine which begins with the incrementing of the speed of the fan 56. P-TEMP is read and the TIME and TEMP values are displayed. A test is initiated to determine whether the Node 6 temperature value has been reached. If the temperature has not been reached then a check is performed to determine whether P-TEMP is greater than or equal to 240° C. If it is the program jumps to the Error Routine. If P-TEMP is not greater than 240° C. then the Node 6 temperature test is repeated. When the Node 6 temperature value is reached a Ready signal occurs which includes the blinking of the warning indicator lamp and the flashing of the TIME and TEMP displays in addition to a repeated audible warning. This step provides a ramping up of the fan speed to begin the cooling of the workpiece. The workpiece can be removed upon hearing the warning "beep".

The Cool Down step of the Thermal Profile Routine, FIG. 12, provides for the cooling of the workstand 12 to receive the next workpiece and to protect the pyrometer 48 from damage due to overheating. P-TEMP is read and the TIME and TEMP values are displayed. A test is initiated to determine whether the current P-TEMP is 20° C. different form the last P-TEMP reading. If not the test is repeated. If the current P-TEMP is 20° C. different from the last P-TEMP an audible warning is sounded and the fan speed is set to medium high to effect cool-down of the workpiece. The indicates that the workpiece was removed from the workstand 12. The program then returns to the Start-up procedures and remains in a wait loop until another workpiece is placed on the treatment platform 46.

The Error Routine, whenever called, simply displays an error code on the LED displays, lowers the heating element 44 and elevator platform 24, and sounds a continuous audible warning. The systems remains in this mode until reset by turning it off and then on again after the workpiece has been removed from the treatment platform 46.

The system operates in accordance with the foregoing program as follows. When a workpiece, which may be a printed circuit board or substrate assembly, is placed on to the target area of the treatment platform 46 the system will begin implementing a predetermined thermal profile or characteristic. Table 1 illustrates an optimum thermal profile for the reflow of SN62 solder paste.

TABLE 1

| Node Point | Temperature [°C.] | Time [Seconds] |
| --- | --- | --- |
| 1 | ambient | 0 |
| 2 | increase to PROGRAM 1 − 11° | 1° C./sec. * |
| 3 | remain at PROGRAM 1 − 11° | 15 |
| 4 | increase to PROGRAM 2 + 14° | X ** |
| 5 | remain at PROGRAM 2 + 14° | 8 |
| 6 | decrease to PROGRAM 1 − 11° | 1.5° C./sec. * |

* time approx. dependent upon material characteristics
** time dependent upon material characteristics In analyzing the thermal profile for SN62 solder paste of Table 1, the workpiece is allowed to increase in temperature at a controlled rate of approximately 1° C./second from Node 1. On reaching Node 2, the temperature, which is based upon the first programmed temperature value, will remain substantially constant below the eutectic point of the solder paste for a defined time interval until reaching Node 3. At this point the solder paste volatiles are volatized and the flux agent has been sufficiently dried. The temperature is then increased at a greater rate than used between Node 1 and Node 2, which rate is entirely dependent on the physical characteristics of the material, until reaching Node 4. The temperature has exceeded the eutectic point of the solder paste and reflow is completed by holding the temperature steady for a defined interval until reaching Node 5. This temperature, based upon the second programmed temperature value, was programmed to be greater than the reflow or melting point of the paste. Now that reflow has occurred, a cooling cycle begins which cools the workpiece at approximately 1.5° C./second. On reaching Node 6 the workpiece is sufficiently cooled below the eutectic point of the solder paste so that it can safely be removed from the workstand 12 without disturbing any of the components now mounted thereon.

The SET switch is used for selecting among several EPROM's containing the predetermined thermal profiles for different materials. The number of depressions of the SET switch will cause the micro-processor to address the selected EPROM and use its contents for the selected thermal profile process.

By controlling and monitoring the thermal profile system parameters by the methods discussed above, a deliberate and accurate thermal profile can be effected upon any material placed in the system. Identical thermal profiles can be implemented and maintained on any process unit regardless of its unit mass or other physical characteristics providing the limitations of the present invention are not exceeded.

It is feasible to expand the methods set forth above to effect a larger scale system. It is also possible to increase the volume processing capacity and to increase the environmental operating temperatures by applying the theory of operation of the present invention to an automated manufacturing line.

The present invention should not be construed as being limited to the application of effecting the reflow of solder paste on a workpiece printed circuit board or substrate. Any material which is susceptible to thermal treating within a predetermined profile or characteristic can be the subject of the thermal treatment described herein.

The present invention may be embodied in other specific forms without departing from the spirit or essential attributes thereof and, accordingly, reference should be made to the appended claims rather than to the specification as indicating the scope of the invention.

I claim:

1. Apparatus for the implementation of a characterized thermal profile of a temperature/time dependent process upon a preselected material or materials comprising:

a substantially rectangular thermally transparent platform capable of supporting the material or materials to be thermally treated having a preselected locus or target area for the placement of said material or materials;

a source of heat energy;

a means for moving said source of heat energy either closer to or farther away from the material or materials to be thermally treated;

a means for creating a controlled air flow through said platform to provide more gradual temperature increases and decreases to the material or materials to be thermally treated;

a temperature measuring means for detecting increases or decreases in the surface temperature of the material or materials to be thermally treated placed in the target area;

a means for storing a predetermined heating and cooling pattern for the material or materials to be thermally treated; and, a means for controlling the thermal treatment of the material or materials to be thermally treated in accordance with the predetermined heating and cooling pattern.

2. Apparatus in accordance with Claim 1 wherein the means for controlling the thermal treatment of the material or materials comprises a means for comparing the emitted surface temperatures of said material or materials to be thermally treated in the target area to temperatures of the predetermined heating and cooling pattern and causing the movement of the source of heat energy closer to or farther away from said material or materials to be thermally treated and the increasing or decreasing of the flow of air in cooperation therewith to effectively achieve the required thermal treatment of the material or materials to be thermally treated all in accordance with the predetermined heating and cooling pattern.

3. Apparatus in accordance with claim 1 wherein the predetermined heating and cooling pattern is dependent upon the thermal characteristics of the material or materials to be thermally treated as perceived by an operator/user and upon the storing of at least two preselected thermal characteristics of the material or materials to be thermally treated in the means for storing the predetermined heating and cooling pattern as a part of said pattern.

4. Apparatus in accordance with claim 1 wherein the means for moving the source of heat energy includes means for fixedly and securedly supporting said source of heat energy.

5. Apparatus in accordance with claim 1 wherein the means for creating a controlled air flow through the platform is a fan.

6. Apparatus in accordance with claim 5 wherein the fan can be incrementally speeded up or slowed down in accordance with the required air flow.

7. Apparatus in accordance with claim 1 wherein the temperature measuring means is an optical pyrometer suitable for operation in the infra-red range.

8. Apparatus in accordance with claim 7 wherein the pyrometer is disposed over the target area at an angle within the range of 30 to 60 degrees above the level of the platform.

9. Apparatus in accordance with claim 7 wherein the pyrometer is disposed over the target area at an angle of 45 degrees above the level of the platform.

10. Apparatus in accordance with claim 1 wherein the temperature measuring means detects the mean or average emitted temperature of the material or materials to be thermally treated.

11. A method for the implementation of a characterized thermal profile of a temperature/time dependent process upon a preselected material or materials comprising the steps of:
  providing a substantially rectangular thermally transparent platform capable of supporting the material or materials to be thermally treated having a preselected locus or target area for the placement of said material or materials;
  providing a source of heat energy;
  providing a means for moving said source of heat energy either closer to or farther away from the material or materials to be thermally treated;
  providing a means for creating a controlled air flow through said platform to provide more gradual temperature increases and decreases to the material or materials to be thermally treated;
  detecting increases or decreases in the surface temperature of the material or materials to be thermally treated placed in the target area by a temperature measuring means;
  storing a predetermined heating and cooling pattern for the material or materials to be thermally treated; and,
  controlling the thermal treatment of the material or materials to be thermally treated in accordance with the predetermined heating and cooling pattern.

12. A method in accordance with claim 11 wherein the controlling of the thermal treatment of the material or materials comprises the further step of comparing the emitted surface temperatures of said material or materials to be thermally treated in the target area to temperatures of the predetermined heating and cooling pattern and causing the movement of the source of heat energy closer to or farther away from said material or materials to be thermally treated and the increasing or decreasing of the flow of air in cooperation therewith to effectively achieve the required thermal treatment of the material or materials to be thermally treated all in accordance with the predetermined heating and colling pattern.

13. A method in accordance with claim 11 wherein the predetermined heating and cooling pattern is dependent upon the thermal characteristics of the material or materials to be thermally treated as perceived by an operator/user and upon the storing of at least two preselected thermal characteristics of the material or materials to be thermally treated in a means for storing the predetermined heating and cooling pattern as a part of said pattern.

14. A method in accordance with claim 11 wherein the detecting of increases or decreases in the surface temperature of the material or materials to be thermally treated comprises the further step of measuring the mean or average emitted temperature of said material or materials.

* * * * *